(12) United States Patent
Brieske

(10) Patent No.: US 10,543,306 B2
(45) Date of Patent: Jan. 28, 2020

(54) APPARATUS FOR MAKING EXTRACORPOREAL BLOOD CIRCULATION AVAILABLE

(71) Applicant: ZOLL LifeBridge GmbH, Ampfing (DE)

(72) Inventor: Gerhard Brieske, Ampfing (DE)

(73) Assignee: ZOLL Circulation, Inc., San Jose, CA (US)

( * ) Notice: Subject to any disclaimer, the term of this patent is extended or adjusted under 35 U.S.C. 154(b) by 0 days.

(21) Appl. No.: 14/018,193

(22) Filed: Sep. 4, 2013

(65) Prior Publication Data
US 2014/0142491 A1 May 22, 2014

Related U.S. Application Data

(63) Continuation of application No. 12/962,615, filed on Dec. 7, 2010, now Pat. No. 8,529,488, which is a
(Continued)

(30) Foreign Application Priority Data

Nov. 24, 2004 (EP) .................................. 04 027 855

(51) Int. Cl.
*A61M 1/34* (2006.01)
*A61M 1/16* (2006.01)
(Continued)

(52) U.S. Cl.
CPC ............ *A61M 1/34* (2013.01); *A61M 1/1698* (2013.01); *A61M 1/32* (2013.01); *A61M 1/3403* (2014.02);
(Continued)

(58) Field of Classification Search
CPC ............ A61M 1/14; A61M 1/16; A61M 1/28; A61M 1/3627; A61M 1/3643;
(Continued)

(56) References Cited

U.S. PATENT DOCUMENTS 3,567,028 A   3/1971   Nose
3,774,762 A   11/1973  Lichtenstein
(Continued)

FOREIGN PATENT DOCUMENTS

DE   1284044 B   11/1968
DE   2138513     3/1972
(Continued)

OTHER PUBLICATIONS

Office Action from corresponding Japanese Patent Application No. 2005-335622 dated Dec. 16, 2009 (4 pages).
(Continued)

*Primary Examiner* — Philip R Wiest
(74) *Attorney, Agent, or Firm* — Robert D. Buyan; Stout, Uxa & Buyan, LLP

(57) ABSTRACT

An apparatus for providing an extracorporeal blood circuit control includes a base module having a control device and a patient module releasably connected to the base module and having blood-conducting components of the extracorporeal blood circuit. A pivot system is also provided at the base module and at the patient module to pivot the patient module relative to the base module about a horizontal axis.

21 Claims, 5 Drawing Sheets

Related U.S. Application Data continuation of application No. 11/284,515, filed on Nov. 22, 2005, now Pat. No. 7,846,122.

(51) Int. Cl.

| | | |
|---|---|---|
| *A61M 1/36* | (2006.01) | |
| *A61M 1/32* | (2006.01) | |
| *A61M 39/28* | (2006.01) | |
| *F04B 43/12* | (2006.01) | |
| *A61M 16/00* | (2006.01) | |
| *F16K 31/00* | (2006.01) | |
| *F16K 35/00* | (2006.01) | |

(52) U.S. Cl.
CPC ........ *A61M 1/3612* (2014.02); *A61M 1/3621* (2013.01); *A61M 1/3626* (2013.01); *A61M 1/3627* (2013.01); *A61M 1/3643* (2013.01); *A61M 1/3644* (2014.02); *A61M 1/3646* (2014.02); *A61M 1/3666* (2013.01); *A61M 1/3693* (2013.01); *A61M 39/281* (2013.01); *F04B 43/12* (2013.01); *A61M 2016/0015* (2013.01); *A61M 2205/3331* (2013.01); *A61M 2205/505* (2013.01); *A61M 2209/08* (2013.01); *F16K 31/00* (2013.01); *F16K 35/00* (2013.01)

(58) Field of Classification Search
CPC .. A61M 2205/12; A61M 1/34; A61M 1/3403; A61M 1/3612; A61M 1/3644; A61M 1/3646; A61M 1/1698; A61M 1/32; A61M 1/3621; A61M 1/3626; A61M 1/3666; A61M 1/3693; A61M 39/281; F04B 43/12
USPC ............. 604/4.01–6.16; 210/321.72–321.79; 422/44–46
See application file for complete search history.

(56) References Cited

U.S. PATENT DOCUMENTS

| | | | |
|---|---|---|---|
| 4,562,984 A * | 1/1986 | Sherlock et al. ............... 248/95 | |
| 4,612,170 A | 9/1986 | Luther et al. | |
| 4,876,066 A * | 10/1989 | Bringham et al. ............. 422/46 | |
| 5,232,437 A | 8/1993 | Lysaght et al. | |
| 5,350,357 A | 9/1994 | Kamen et al. | |
| 5,950,670 A | 9/1999 | Flaim | |
| 6,071,257 A | 6/2000 | Stojanovic | |
| 6,071,258 A | 6/2000 | Dalke et al. | |
| 6,695,803 B1 * | 2/2004 | Robinson et al. ........... 604/4.01 | |
| 6,748,815 B2 | 6/2004 | Povey et al. | |
| 7,367,540 B2 | 5/2008 | Brieske | |
| 7,597,546 B2 | 10/2009 | Brieske | |
| 2002/0085952 A1 * | 7/2002 | Ellingboe ........... A61M 1/3621 422/45 |
| 2002/0176798 A1 * | 11/2002 | Linker et al. ................... 422/45 | |
| 2004/0069709 A1 * | 4/2004 | Brugger et al. .............. 210/646 | |
| 2005/0004480 A1 | 1/2005 | Kirchhof | |
| 2006/0122551 A1 | 6/2006 | Brieske | |
| 2007/0146342 A1 | 6/2007 | Medler et al. | |
| 2008/0171960 A1 | 7/2008 | Brieske et al. | |

FOREIGN PATENT DOCUMENTS

| | | | | |
|---|---|---|---|---|
| DE | 3834952 A1 | 4/1989 | | |
| DE | 19534502 A1 | 3/1997 | | |
| DE | 29719899 U1 | 2/1998 | | |
| DE | 19702098 A1 | 7/1998 | | |
| DE | 19905937 C1 | 7/2000 | | |
| EP | 0171749 A1 | 2/1986 | | |
| EP | 0223864 A1 | 6/1987 | | |
| EP | 1661592 A1 | 5/2006 | | |
| FR | 2368284 | 5/1978 | | |
| JP | 2002527212 A | 8/2002 | | |
| JP | 2002536126 A | 10/2002 | | |
| JP | 2003-180824 | * | 7/2003 | .............. A61M 1/14 |
| JP | 2003180824 A | 7/2003 | | |
| WO | 9511709 A2 | 5/1995 | | |
| WO | 0023140 A1 | 4/2000 | | |
| WO | 0047248 A1 | 8/2000 | | |
| WO | 0226288 A2 | 4/2002 | | |
| WO | 2004098678 A1 | 11/2004 | | |

OTHER PUBLICATIONS

United States Patent & Trademark Office, Office Action dated Apr. 21, 2010 in U.S. Appl. No. 11/284,515, 11 pages.
United States Patent & Trademark Office, Final Office Action dated Dec. 8, 2009 in U.S. Appl. No. 11/284,515, 10 pages.
United States Patent & Trademark Office, Office Action dated May 27, 2009 in U.S. Appl. No. 11/284,515, 13 pages.
European Patent Office, Decision to Grant dated May 6, 2008 in European Patent Application No. EP04027855.8, 2 pages.
European Patent Office, European Search Report dated Aug. 10, 2007 in European Patent Application No. EP07010455.9, 7 pages.
European Patent Office, Translation of European Search Reprot dated Apr. 20, 2005, in European Patent Application No. EP04027855.8, 4 pages.
United States Patent & Trademark Office, Notice of Allowance dated Oct. 4, 2010in U.S. Appl. No. 11/284,515, 8 pages.

* cited by examiner

APPARATUS FOR MAKING EXTRACORPOREAL BLOOD CIRCULATION AVAILABLE

CROSS-REFERENCE TO RELATED APPLICATIONS

This application is a continuation of U.S. patent application Ser. No. 12/962,615 filed Dec. 7, 2010 and issued on Sep. 10, 2013 as U.S. Pat. No. 8,529,488, which is a continuation of U.S. patent application Ser. No. 11/284,515 filed Nov. 22, 2005 and issued on Dec. 7, 2010 as U.S. Pat. No. 7,846,122, which claims priority to European Patent Application No. EP 04 027 855.8 filed on Nov. 24, 2004, the entire disclosure of each such prior application being expressly incorporated herein by reference.

FIELD OF THE INVENTION

The present invention relates to an apparatus for the provision of an extracorporeal blood circuit, in particular heart-lung machines, comprising at least one base module having a control device and a patient module releasably connected to the base module and having blood-conducting components of the extracorporeal blood circuit.

BACKGROUND OF THE INVENTION

Heart-lung machines of this type are known, for example, as portable devices for emergency use. It is a problem in this respect that it must be ensured with devices of this type prior to the putting into operation that there is no longer any air in the blood-conducting components of the extracorporeal blood circuit, since this could seriously endanger a patient. A so-called priming liquid is therefore filled in and the extracorporeal blood circuit is vented or deaerated prior to the putting into operation in order to eliminate the air bubbles present in the blood-conducting components. This is, however, time-consuming with the known apparatus.

SUMMARY OF THE INVENTION

It is an object of the present invention to provide an apparatus of the initially named kind with which the venting of a patient module filled with priming liquid can take place in a short time.

This object is satisfied in particular in that pivot means are provided at the base module and/or at the patient module to pivot the patient module relative to the base module about a horizontal axis from a filling position into an operating position.

The patient module can be pivoted in a guided manner relative to the base module by the pivot means provided in accordance with the invention, whereby the position and orientation of individual components of the extracorporeal blood circuit is modified so that air bubbles which cannot escape in the filling position due to the design can be removed from the system at or after the transition to the operating position via venting lines.

The filling and venting of a patent module can take place in a time period in the order of magnitude of approximately 2 minutes due to the pivot means in accordance with the invention, whereas comparable apparatus in accordance with the prior art require approximately 20 minutes for this procedure, which can be decisive in emergency situations.

Advantageous embodiments of the invention are described in the description, in the drawing and in the dependent claims.

In accordance with a first advantageous embodiment, there is approximately 90.degree. between the filling position and the operating position, which has the advantage that any air bubbles can reliably escape from the blood-conducting components.

In accordance with a further advantageous embodiment, a blood reservoir is provided in the patient module and is arranged at an inclination of approximately 45.degree. to the horizontal both in the filling position and in the operating position. This has the consequence that the blood reservoir again has the same orientation relative to the horizontal after a rotation of the patient module by 90.degree. so that the same flow conditions result inside the reservoir before and after the pivoting.

In accordance with a further advantageous embodiment, a centrifugal pump head having a central inlet and a tangential outlet can be arranged in the patient module such that the inlet is oriented vertically upwardly in the filling position and horizontally in the operating position. In this manner, the pump head can be filled with priming liquid from above without air bubbles remaining in the pump head in this process. It can likewise be advantageous in this process to provide the centrifugal pump head with a tangential outlet which is arranged at the bottommost position of the centrifugal pump head in the operating position. It is ensured in this manner that no air is pumped inside the intracorporeal blood circuit by the centrifugal pump in operation.

In accordance with a further advantageous embodiment, an arterial filter having a venting outlet can be arranged in the patient module such that the venting outlet is oriented horizontally in the filling position and vertically upwardly in the operating position. The possibility hereby in turn results that air inside the arterial filter, which is still present in the filter after the filling with priming liquid, can escape upwardly via the venting outlet after a pivoting into the operating position.

The pivot means provided in accordance with the invention can be provided in the most varied designs and can in particular include a mount for the patient module pivotally supported at the base module. In this case, the patient module only has to be coupled to the mount in order to permit a guided pivot movement. It is particularly advantageous in this process for the pivot means to include a guide provided at the mount and at the patient module. In this case, the patient module can also be used to ensure the guided pivot movement.

It is alternatively possible to connect the patient module to a further module, for example to a control module, and to fasten the unit of patient module and control module to the mount. In this case, the guide can be provided at the mount and at the control module.

It is also possible, for example, to provide a pivot bearing at the base module into which the other module or other modules are inserted.

The patient module is preferably in the operating position after being placed onto the base module since, in this case, a fast removal of the patient module from the base module is ensured without a pivoting having to be carried out beforehand.

In accordance with a further advantageous embodiment, the base module has a device stand which is provided with a pivotal hook to hang the apparatus on the frame of a patient's bed.

In accordance with a further aspect of the invention, it relates to a method for the putting into operation of an apparatus of the aforementioned type, with the patient module first being brought into the filling position in which filling position the blood-conducting components are filled with a priming liquid, with the patient module subsequently being pivoted relative to the base module, in particular by 90.degree., into the operating position. The advantages described above result with such a method.

In accordance with an advantageous method variant, a pump head provided in the patient module can be driven prior to the pivoting in order to pump the already filled-in priming liquid and thereby to further vent the blood-conducting components.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The present invention will become more fully understood from the detailed description and the accompanying drawings, wherein.

DETAILED DESCRIPTION OF THE PREFERRED EMBODIMENTS

The following description of the preferred embodiment(s) is merely exemplary in nature and is in no way intended to limit the invention, its application, or uses.

The heart-lung machine shown in FIGS. 1 to 4, is composed of three modules, namely a base module B provided with a device stand 10, a control module S and a patient module P which has blood-conducting components of an extracorporeal blood circuit.

In the embodiment shown, the patient module P is coupled via latch elements (not shown) to the control unit S to form a unit and this unit, consisting of the control module S and the patient module P is releasably latched to a mount 12 of the base module B.

Figure 1:
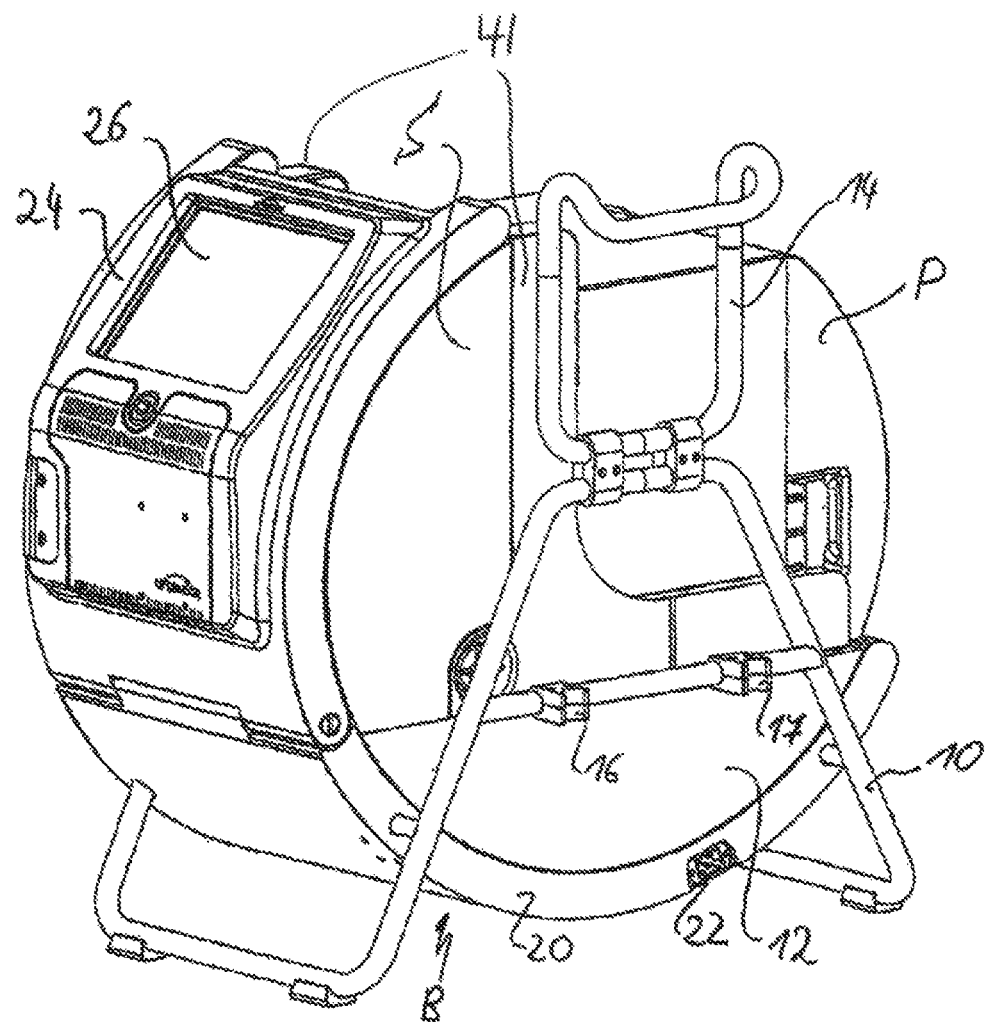
FIG. 1 is a perspective view of a portable heart-lung machine.

As FIG. 1 shows, the device stand 10 made from tubular material has a pivotal hook 14 at its upper side which is bent to form a hook at its upper side to permit a hanging to a frame of a patient's bed. The pivotal hook 14 can be pivoted downwardly by 180.degree. from the position shown in FIG. 1 and can be plugged into two holding clips 16, 17 so that the pivotal hook 14 is not in the way on the mounting of the control module S and of the patient module P.

The device stand 10 is fixedly connected to a carrier element 20 of the base module B which has a plug socket 22 for a mains cable. The mount 12 is furthermore pivotally supported in the carrier element 20, as will be explained in more detail in the following.

An operating part 24 is foldably fastened to the left hand side of the carrier element 20 in FIG. 1 and has a touch screen 26 which represents an input and output means for a control device (computer) provided in the base module. As the Figure furthermore shows, the carrier element 20 and the non-folded operating part 24 form an annular jacket for the unit of mount 12, control module S and patient module P. The operating part 24 must be folded open to the left from the position shown in FIG. 1 to mount or remove the unit of control module S and patient module P.

Figure 2:
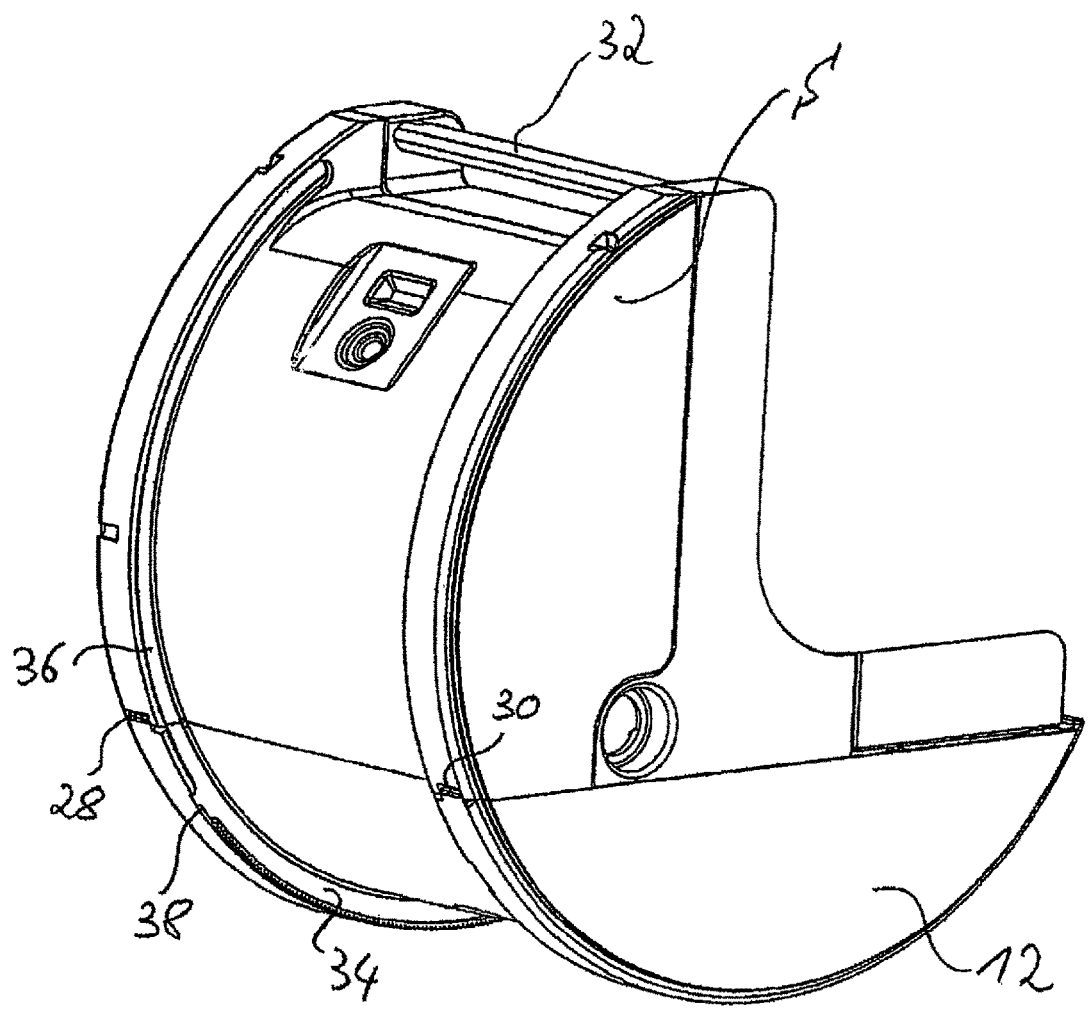
FIG. 2 is a perspective view of the control module of the heart-lung machine of FIG. 1 connected to a mount of the base module.

FIG. 2 shows the mount 12 of the base module B of FIG. 1 to which the control module S is releasably connected by means of latch connections 28, 30. The patient module P is not shown in FIG. 2 for a simplified representation. It must, however, be pointed out that a unit of control module S and patient module P is always plugged onto or removed from the mount 12 in operation.

As FIG. 2 further shows, the control module S supplements the disk-segment shaped geometry of the mount 12 and a handle 32 is located at the upper side of the control module S with which the unit of control module S and patient module P, on the one hand, but also the whole heart-lung machine, on the other hand, can be handled when the three modules are fastened to one another as shown in FIG. 1.

To pivot the patient module P only not shown in FIG. 2 relative to the base module B about a horizontal axis from a filling position into an operating position, the mount 12 of the base module B is equipped with two guide rails 34 which are parallel, provided at the outer periphery and cooperate with adjoining guide rails 36 of the control module S. The guide rails 34 and 36 form a continuous guide structure with the aid of which the unit of mount 12, control module S and patient module P can be pivoted relative to the base module B.

As FIG. 2 shows, the guide rails 34 of the pivot mount 12 are provided with a cut-out 38 with whose aid the pivot mount 12 can be guided over two rollers (not shown) provided at the carrier element 20 so that the pivot mount 12 can be pivoted on the support element 20 of the base module B. The toothed arrangement recognizable in FIG. 2 serves for the engagement of a damping mechanism ensuring a uniform and damped pivot movement.

To assemble the pivot mount 12 with the support element 20, the pivot mount 12 is first brought into a substantially vertical position and the cut-outs 38 are guided via the rollers (not shown) provided at the carrier element 20, whereupon the pivot mount 12 can subsequently be pivoted into the position shown in FIG. 1. After the folding open of the operating part 24, the previously assembled unit of control module S and patient module P can be latched on the pivot mount 12. To pivot the patient module P from the now present operating position into a filling position, the now formed unit of control module S, patient module P and pivot mount 12 can be pivoted by 90.degree. by pivoting down the handle 32 so that the control module S is in the position in which the pivot mount 12 was previously located. In this filling position, the blood-conducting components of the patient module P are in the position and orientation shown in FIG. 3 with respect to the horizontal.

Figure 3:
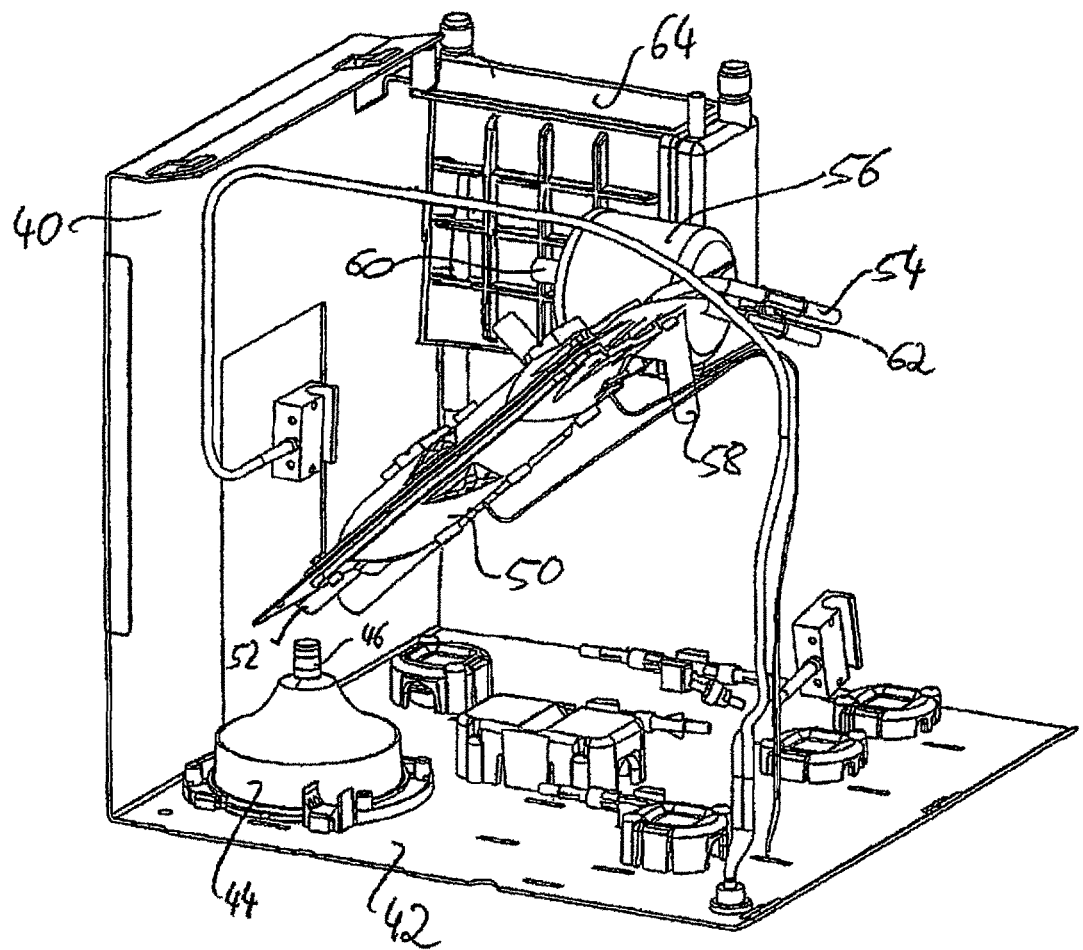
FIG. 3 is a perspective view of some blood-conducting components of the patient module in the filling position.

FIG. 3 shows some blood-conducting components of the patient module, with the patient module P having been rotated about 90.degree. counterclockwise, starting from FIG. 1. The view shown in FIG. 3 corresponds to a view from other side of the patient module P in comparison with FIG. 1. The wall 40 of the patient module P standing perpendicular in FIG. 3 is thus disposed parallel next to the pivot mount 12, whereas the horizontally oriented wall 42 adjoins the control module S. Furthermore, a plurality of hose connections are now shown in FIG. 3 for a better clear view.

Figure 4:
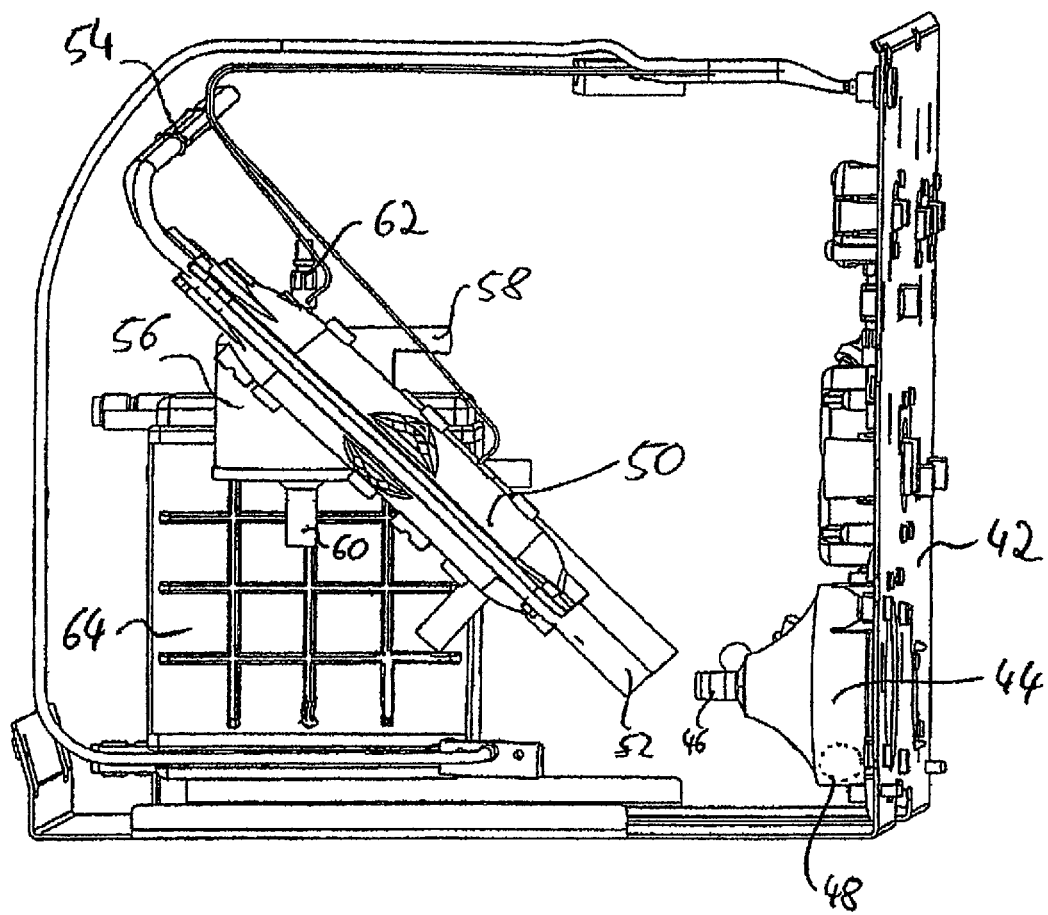
FIG. 4 is the representation of FIG. 3 in the operating position, but in a view from the rear.

In FIG. 3, the reference numeral 44 designates a centrifugal pump head having a central suction inlet 46 and a radial outlet 48 shown by broken lines in FIG. 4.

Furthermore, an approximately parallelepiped shaped blood reservoir 50 is installed at a position of 45.degree. in the patient module P and its outlet 52 is connected to the inlet 46 of the centrifugal pump head 44 via a hose line (not shown). Venting lines 54 are located at the upper side of the blood reservoir 50. The inlet into the blood reservoir 50 coming from a venous connection is arranged approximately at the centre of the blood reservoir and cannot be recognized in FIGS. 3 and 4.

Furthermore, it can be recognized in FIGS. 3 and 4 that an arterial filter 56 is provided in the patient module P which has a cylindrical shape, with a tangential inlet 58 and a central axial outlet 60 being provided. A venting connection 62 is provided centrally at the end face of the filter disposed opposite the outlet 60.

Further components shown of the patient module P are an oxygenator 64 and various connection elements which are provided at the wall 42 disposed adjacent to the control module S and which serve for the cooperation with terminals, sensors or plug connections, since all blood-conducting components are provided in the patient module P, whereas control components such as the pump drive, valves and other electrical control elements are arranged in the control module S.

FIG. 4 shows the representation of FIG. 3 in the operating position which corresponds to the representation of FIG. 1 in which the control module S and the wall 42 of the patient module P contacting it are oriented vertically. The patient module P is positioned between guide members 41 which extend from the control module S.

As a comparison of FIGS. 3 and 4 shows, there is 90.degree. between the filling position (FIG. 3) and the operating position FIG. 4), with the blood reservoir 50 provided in the patient module P being arranged in both positions at an inclination of 45.degree. to the horizontal, since it is installed at 45.degree. in the patient module. The centrifugal pump head 44 is arranged such that the central inlet 46 is oriented vertically upwardly in the filling position (FIG. 3) and horizontally to the side in the operating position (FIG. 4). The outlet 48 (not recognizable in FIG. 3) of the pump head 44 is arranged at the bottommost position of the centrifugal pump head 44 in the operating position shown in FIG. 4 so that the outlet 48 lies beneath the inlet 46.

The arterial filter 56 is also arranged within the patient module such that the venting outlet 62 is oriented horizontally in the filling position and vertically upwardly in the operating position (FIG. 4). The inlet 58 is oriented vertically downwardly in the filling position and horizontally in the operating position, whereas the outlet 60 is oriented horizontally in the filling position and vertically downwardly in the operating position.

Figure 5:
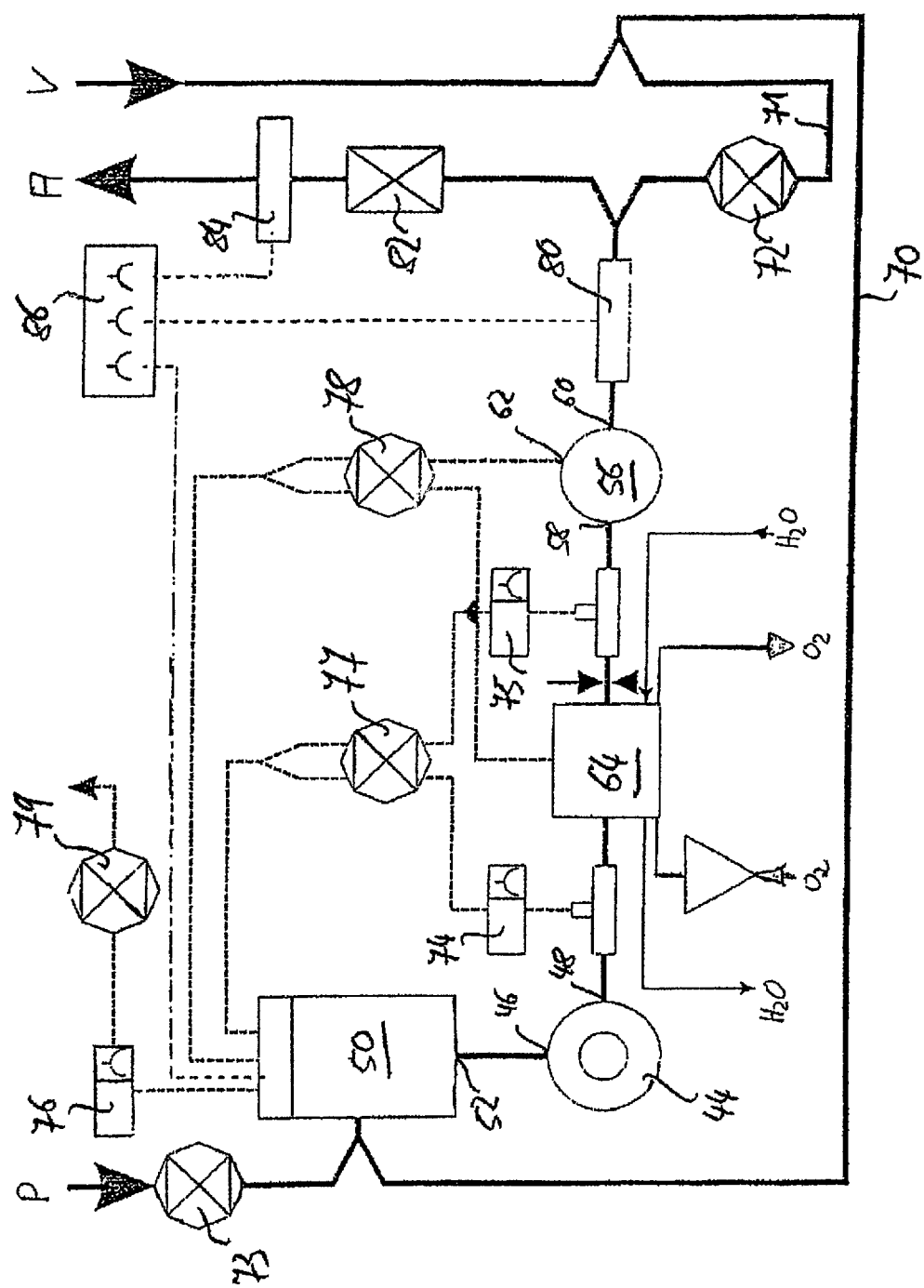
FIG. 5 is a diagram showing the individual components of the heart-lung machine.

FIG. 5 shows the different components of the heart-lung machine in accordance with the invention in which the patient blood coming from a venous connection V is guided via a line 70 into the blood reservoir 50 and flows from there via the outlet 52 into the inlet 46 of the centrifugal pump 44. It is pumped from there via the outlet 48 into the oxygenator 64 and flows from there via the arterial filter 56 to the arterial connection A and from there back into the body of the patient. An internal bypass which can be switched via a valve 72 is designated by reference numeral 71. Reference numeral 73 designates a valve for the inflow line PR with which priming liquid can be guided into the circuit. Reference numerals 74, 75 and 76 each designate pressure sensors. Venting valves are designated by reference numerals 77, 78 and 79, with the valves 77 and 78 switching the vent paths into the upper region of the blood reservoir 50 not filled with blood and the venting valve 79 controlling the venting from the blood reservoir. Reference numeral 80 designates a bubble sensor which controls a fast-closing valve 82 provided in the arterial outlet A if air bubbles are detected. Reference numeral 84 designates a flow sensor and reference numeral 86 an electrical interface.

As the Figure furthermore shows, the oxygenator 64 is provided with inflow lines and outflow lines for water and oxygen to effect an enriching of the blood with oxygen and a temperature control of the blood.

To put the heart-lung machine described above into operation, starting from the representation of FIG. 1, the pivotal hook 14 is first pivoted downwardly by 180.degree. and the operating part 24 is folded to the left. Subsequently, the total unit consisting of the control module S, the patient module P and the pivot mount 12 can be pivoted counter-clockwise so that the filling position is reached.

Priming liquid, which first (cf. FIG. 5) fills the blood reservoir and from there the centrifugal pump head 44, is supplied via the connection PR in the filling position. The air located in the hosing is largely removed from the system in this process by the priming liquid arranged above the machine on filling, with air bubbles, however, remaining in the upper region of the arterial filter 56 and in horizontal line portions.

When the blood reservoir 50 is almost filled, the centrifugal pump head 44 is set into rotation comparatively slowly, whereby the priming liquid is pumped through the system and further air residues are removed from the system. After a time period: of approximately 20 seconds, further components—such as the oxygenator 64—are also filled with priming liquid so that the pump can be stopped and the unit of the control module S, patient module P and pivot mount 12 can be pivoted back into the operating position. After these pivoting back by 90.degree., that air can also escape which had remained in the arterial filter 56 and in horizontal line portions. A complete filling and venting of the patient module can thus be achieved within a time period in the order of magnitude of approximately 2 minutes.

The description of the invention is merely exemplary in nature and, thus, variations that do not depart from the gist of the invention are intended to be within the scope of the invention. Such variations are not to be regarded as a departure from the spirit and scope of the invention.

What is claimed is:

1. A system useable for extracorporeal oxygenation of a patient's blood comprising a re-useable control module and at least one patient module, the patient module being positionable on the control module and useable for performing a blood oxygenating procedure in a patient, then thereafter removable from the control module and replaceable by another patient module useable for performing another blood oxygenating procedure in another patient;

wherein the re-useable control module comprises a housing which contains non-blood-contacting components including a power source, a controller, and circuitry; and wherein the patient module comprises a venous blood inlet flow path for carrying deoxygenated blood from the patent's vasculature into the patient module, an oxygenated blood outlet flow path for carrying oxygenated blood from the patient module back into the patient and blood-contacting processing components, namely; a blood reservoir configured to separate air bubbles from blood such that separated air collects in an air collection region of the reservoir, a vent line connected to the air collection region of the reservoir, said pump head having a central inlet in a top portion of the pump head and a an outlet in a bottom portion of the pump head, said pump head being positioned in the patient module such that the central inlet receives blood from a blood outlet in a bottom end of the reservoir and the pump head outlet is connected to a blood inlet of the oxygenator; a blood filter, an oxygenator, and an air bubble sensor for detecting air bubbles in the oxygenated blood outlet flow path, said patient module further comprising a fast-closing valve on the oxygenated blood outlet flow path downstream of the bubble sensor and a bypass flow path that is connected to a location on the oxygenated blood outlet flow path downstream of the air bubble sensor but upstream of the fast-closing valve and extends to a location on the venous blood inlet flow path, and a bypass valve on the bypass flow path, wherein all of said blood-contacting components other than said fast-closing valve are located upstream of the location at which the bypass flow path is connected to the oxygenated blood outlet flow path;

wherein, during operation of the system, upon detection of a bubble by the bubble detector, the fast closing valve is closed and the bypass valve is opened, thereby causing blood and the air bubble that has been detected by the air bubble sensor to recirculate from said location on the oxygenated blood outlet flow path through the bypass flow path and into the venous blood inlet flow path; and wherein the patient module comprises connection elements located on a wall of the patient module and the control module comprises corresponding connection elements on the housing of the control module housing; and wherein the system comprises guide members which facilitate placement of the patient module at an operating position on the control module whereby the connection elements on the wall of the patient module become engaged with the corresponding connection elements of the control module such that:

sensor signals are transmitted from the bubble sensor of the patient module to the controller of the control module;

control signals are transmitted from the controller of the control module to the fast closing valve and bypass valve of the patient module; and the pump drive engages the pump head so as to drive the pump head in a manner that pumps blood from the reservoir to the oxygenator and through the blood contacting components and oxygenated blood outlet flow path downstream of the oxygenator.

2. A system according to claim 1 wherein the patient module is capable of being primed with fluid, vented and ready for use within 2 minutes.

3. A system according to claim 1 wherein the base unit electrical contacts and patient module electrical contacts are selected from terminals, sensors and plug connections.

4. A system according to claim 3 wherein the pump head comprises a centrifugal pump head.

5. A system according to claim 4 wherein the centrifugal pump head has a central blood inlet and a tangential blood outlet.

6. A system according to claim 1 wherein the user input and output apparatus comprises a touch screen.

7. A system according to claim 1 further comprising latches for attaching the patient module to the base unit so that the electrical contacts are properly engaged to transmit control signals from the base unit to the patient module and sensor signals from the patient module to the base unit and the pump drive engages the pump head so as to drive the pump head in a manner that pumps blood from the reservoir to the oxygenator and through the blood contacting components and oxygenated blood outlet flow path downstream of the oxygenator.

8. A system according to claim 1 wherein the patient module latches to the control module when in the operating position.

9. A system according to claim 1 further comprising a base module which comprises pivot means useable to move the patient module back and forth between a filling position and an operating position.

10. A patient module for an extracorporeal blood oxygenating system, said patient module comprising a housing which contains a venous blood inlet conduit, and arterial blood outlet conduit, and blood-contacting processing components, namely; a blood reservoir, an oxygenator, a pump head positioned below the reservoir, said pump head having a central inlet in a top portion thereof a tangential outlet in a bottom portion thereof, said tangential outlet being connected to the oxygenator; an air bubble sensor on the arterial blood outlet conduit, and a fast closing valve on the arterial outlet conduit downstream of the bubble sensor, said patient module further comprising a bypass conduit that is connected to a location on the arterial blood outlet conduit downstream of the air bubble sensor but upstream of the fast closing valve and extends to a location on the venous inlet conduit, and a bypass conduit valve, wherein all of said blood-contacting processing components other than said fast-closing valve are located upstream of the location at which the bypass flow path is connected to the arterial blood outlet conduit, said patient module further comprising connection elements located on a wall of the patient module;

wherein the patient module is configured to be advanced along guide members to an operating position in which the connection elements located on a wall of the patient module become engaged with the corresponding connection elements on a control module which comprises a power source, controller and pump drive such that:

sensor signals are transmitted from the air bubble sensor of the patient module to the controller of the control module;

control signals are transmitted from the controller of the control module to the fast closing valve and bypass valve of the patient module; and the pump drive engages the pump head so as to drive the pump head in a manner that pumps blood from the reservoir to the oxygenator and through the blood contacting components and oxygenated blood outlet flow Path downstream of the oxygenator.

11. A patient module according to claim 10 configured to be attached to a base unit, primed with fluid, vented and ready for use within 2 minutes.

12. A patient module according to claim 10 wherein said electrical contacts are selected from terminals, sensors and plug connections.

13. A method for extracorporeal oxygenation of a patient's blood, said method comprising the steps of:
   a) providing or obtaining a patient module according to claim 10;
   b) advancing the patient module along said guide members to said operating position in which the connection elements located on a wall of the patient module become engaged with the corresponding connection elements on a control module;
   c) priming and venting the patient module;
   d) connecting the venous blood inlet flow path to the venous vasculature of the patient and connecting the oxygenated blood outlet flow path to the arterial vasculature of the patient; and
   e) operating the system so that venous blood enters through the venous blood inlet conduit, circulates through the blood-contacting processing components with the blood becoming oxygenated by the oxygenator and the oxygenated blood then is then returned to the patient through the arterial blood outlet conduit, with the bubble sensor sensing for bubbles in the oxygenated blood and, upon detection of a bubble by the bubble detector, the fast closing valving device closes, the bypass conduit valve opens and the blood pumping apparatus continues to operate so as to cause the blood and the air bubble that has been detected by said bubble sensor to circulate through the bypass conduit, into the venous blood inlet flow path and through the reservoir wherein the detected bubble will separate from the blood.

14. A method according to claim 13 further comprising the steps of:
   f) disconnecting the venous blood inlet from the patient's venous vasculature and disconnecting the arterial blood outlet from the patient's arterial vasculature; and
   g) disconnecting and removing the patient module from the base unit.

15. A method according to claim 13 wherein the priming and venting of the patient module is carried out within two minutes.

16. A method according to claim 13 wherein the patient module latches to the control module and wherein Step b further comprises latching the patient module to the control module while in said operating position.

17. A method according to claim 13 further comprising:
   prior to Step c, pivoting the patient module to a filling position; and
   prior to Step d, pivoting the patient module from the filling position to an operating position.

18. A system comprising a patient module according to claim 10 in combination with the control module, wherein the patient module latches to the control module when positioned in the operating position.

19. A system comprising a patient module according to claim 10 in combination with a unitary control module and a base module which comprises pivot means useable to move the patient module back and forth between a filling position and an operating position.

20. A patient module according to claim 10 wherein the pump head comprises a centrifugal pump head.

21. A patient module according to claim 20 wherein the centrifugal pump head has a central blood inlet and a tangential blood outlet.

* * * * *